US009289202B2

(12) United States Patent
Martin

(10) Patent No.: US 9,289,202 B2
(45) Date of Patent: Mar. 22, 2016

(54) SUTURE-RETAINING DEVICE AND ANCHOR

(75) Inventor: Daniel L. Martin, Palo Alto, CA (US)

(73) Assignee: Syntorr, Inc., Palo Alto, CA (US)

( * ) Notice: Subject to any disclaimer, the term of this patent is extended or adjusted under 35 U.S.C. 154(b) by 1044 days.

(21) Appl. No.: 12/540,628

(22) Filed: Aug. 13, 2009

(65) Prior Publication Data

US 2010/0036416 A1    Feb. 11, 2010

Related U.S. Application Data

(63) Continuation-in-part of application No. 12/187,325, filed on Aug. 6, 2008, now abandoned.

(51) Int. Cl.
*A61B 17/04* (2006.01)
*A61F 2/08* (2006.01)
*A61B 17/72* (2006.01)
*A61B 17/00* (2006.01)

(52) U.S. Cl.
CPC .......... *A61B 17/0401* (2013.01); *A61B 17/7233* (2013.01); *A61F 2/0811* (2013.01); *A61B 17/7225* (2013.01); *A61B 2017/00862* (2013.01); *A61B 2017/0403* (2013.01); *A61B 2017/044* (2013.01); *A61B 2017/0417* (2013.01); *A61B 2017/0445* (2013.01); *A61B 2017/0453* (2013.01); *A61F 2002/087* (2013.01); *A61F 2002/0829* (2013.01); *A61F 2002/0841* (2013.01); *A61F 2002/0882* (2013.01)

(58) Field of Classification Search
CPC ............... A61B 17/0401; A61B 2017/044; A61B 2017/0445; A61B 2017/0453; A61B 2017/0441; A61B 2002/0829; A61B 2002/0841; A61B 2002/087; A61B 17/7225; A61B 17/7223; A61F 2002/0882; A61F 2/0811
USPC ............................ 606/72, 139, 144, 148, 232
See application file for complete search history.

(56) References Cited

U.S. PATENT DOCUMENTS

| | | | | |
|---|---|---|---|---|
| 4,960,420 A * | 10/1990 | Goble et al. | | 606/232 |
| 5,593,410 A * | 1/1997 | Vrespa | | 606/312 |
| 5,860,978 A * | 1/1999 | McDevitt et al. | | 606/232 |
| 6,302,886 B1 * | 10/2001 | McDevitt et al. | | 606/232 |
| 6,491,714 B1 * | 12/2002 | Bennett | | 606/232 |
| 6,565,573 B1 * | 5/2003 | Ferrante et al. | | 606/62 |
| 2002/0156476 A1 * | 10/2002 | Wilford | | 606/72 |
| 2003/0130694 A1 * | 7/2003 | Bojarski et al. | | 606/228 |
| 2003/0144696 A1 * | 7/2003 | Sinnott et al. | | 606/232 |
| 2004/0093030 A1 * | 5/2004 | Cox et al. | | 606/232 |
| 2004/0097945 A1 * | 5/2004 | Wolf | | 606/73 |
| 2005/0245932 A1 * | 11/2005 | Fanton et al. | | 606/72 |
| 2005/0283158 A1 * | 12/2005 | West, Jr. | | 606/73 |
| 2006/0079904 A1 * | 4/2006 | Thal | | 606/72 |
| 2006/0241657 A1 * | 10/2006 | Cerundolo | | 606/148 |
| 2006/0247641 A1 * | 11/2006 | Re et al. | | 606/72 |

* cited by examiner

*Primary Examiner* — Alexander Orkin
(74) *Attorney, Agent, or Firm* — Patterson & Sheridan, LLP

(57) ABSTRACT

A rotator cuff tendon injury is repaired using a flexible fastener and an anchor. The flexible fastener is attached to the rotator cuff tendon and also secured to the anchor. The anchor is attached to or supported by various locations on the humerus other than the humeral head, to provide a robust means for holding the rotator cuff tendon in the desired position against the humeral head.

8 Claims, 15 Drawing Sheets

SUTURE-RETAINING DEVICE AND ANCHOR

CROSS-REFERENCE TO RELATED APPLICATIONS

This application is a continuation-in-part of U.S. patent application Ser. No. 12/187,325, filed Aug. 6, 2008 now abandoned.

BACKGROUND OF THE INVENTION

1. Field of the Invention

Embodiments of the present invention relate generally to surgical repair of the rotator cuff tendon and, more particularly, to devices and methods used in repairing the rotator cuff tendon that has been detached from the humeral head.

2. Description of the Related Art

In surgeries involving repair of a rotator cuff tendon that has been detached from the humeral head, the tendon must be artificially pressed against the humeral head in order to allow the tendon to naturally re-attach to the underlying bone over time. FIGS. 1 and 2 illustrate two prior art techniques for repairing a rotator cuff tendon that has been detached from the humeral head.

FIG. 1 schematically illustrates a rotator cuff tendon 101 secured to a humeral head 102 of a humerus 100 by a plurality of suture anchors 103. Suture anchors 103 are positioned so that sutures 104, which are sewn into rotator cuff tendon 101, position the tendon against region 105 of humeral head 102, where region 105 approximates the original anatomic attachment region of rotator cuff tendon 101, often referred to as the "footprint." In this way, rotator cuff tendon 101 will grow onto region 105, forming a new bond between rotator cuff tendon 101 and humeral head 102. Issues associated with the use of the technique illustrated in FIG. 1 include anchor displacement, "lift-off" of the rotator cuff tendon, the availability of a limited number of sutures to secure rotator cuff tendon 101 to humeral head 102, and the inability to perform this surgery because rotator cuff tendon 101 has retracted too far away from the original anatomic attachment location of rotator cuff tendon 101.

The bone making up humeral head 102 near the footprint of the rotator cuff provides a relatively weak base for the insertion of suture anchors 103, since this portion of humerus 100 is relatively porous and soft. Because of this, adequate fixation of suture anchors 103 is problematic. Namely, anchor displacement from the supporting bone is a common failure mechanism of suture anchors 103, and results from localized fracturing of the surrounding bone material.

Suture anchors 103, when positioned as shown, hold rotator cuff tendon 101 against region 105. However, when the arm containing humerus 100 is raised, "lift-off" of rotator cuff tendon 101 from region 105 may occur, i.e., rotator cuff tendon 101 is temporarily pulled out of contact with region 105. Lift-off is known to inhibit the re-attachment and healing of rotator cuff tendon 101.

The number of suture anchors that can be used is limited. This is due to the limited area of humeral head 102 in which suture anchors 103 are placed. Also, the placement of many suture anchors 103 is time consuming and tedious for the surgeon. As a consequence, a small number of larger sutures are typically used with suture anchors, leading to very large knot volumes. Very large knot volumes result because the knot volume of a suture is roughly proportional to the cube of the suture diameter. Large knots on the surface of the rotator cuff are undesirable as they rub against the overlying acromial bone. Furthermore, fewer sutures provide a less robust connection between rotator cuff tendon 101 and humeral head 102. For a given surgical application, a large number of small diameter sutures are superior to a few large sutures, in terms of holding power in the tissue.

In some situations, bone tunnels may be used to attach sutures to bone and thereby properly position a tendon to be repaired. FIG. 2 schematically illustrates a bone tunnel 203 formed through a humeral head 202 of a humerus 200 after removal of bone material from the humeral head 202. Bone tunnel 203 is formed so that sutures 204, which are sewn into rotator cuff tendon 201, may be threaded through holes formed in a bone structure 206 and thereby position rotator cuff tendon 201 against region 205 for proper healing. A key limitation of this technique is that an already weak bone structure 206 is further weakened as a result of thread holes formed for sutures 204 and is susceptible to breakage before rotator cuff tendon 201 is sufficiently healed.

SUMMARY OF THE INVENTION

The present invention provides devices and methods used in repairing the rotator cuff tendon. A device according to an embodiment of the invention comprises a suture-retaining device to which multiple sutures sewn into a rotator cuff tendon are to be attached and an anchor that is mechanically coupled to the suture-retaining device. The anchor has a threaded end configured for engagement with a cortex of the humerus to provide firm support for the suture-retaining device. The anchor generally approaches the cortex from the endosteal side. The method according an embodiment of the invention includes the steps of providing a flexible fastener and an anchor, attaching the flexible fastener to the rotator cuff tendon and the anchor, and securing the anchor at various locations on the humerus other than the humeral head.

A device for supporting sutures, according to another embodiment, comprises a head portion for engagement with a plurality of sutures and an adjustable length body portion having a threaded end for engagement with a bone. The adjustable length body portion may comprise a cannulated screw having the threaded end and an internal threaded portion, and a secondary screw engaged with the internal threaded portion and attached to the head portion.

A method for repairing a rotator cuff tendon that has detached from a head of a humerus, according to another embodiment of the invention, comprises the steps of anchoring a screw in a cortex of the humerus and attaching a plurality of sutures that have been sewn into the rotator cuff tendon to a suture-retaining device that is mechanically coupled to the screw. The inventive method may further comprise the step of adjusting the position of the suture-retaining device.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

Embodiments of the invention contemplate devices and methods used in repairing the rotator cuff tendon that has been detached from the humeral head. A device according to one embodiment of the invention comprises a suture-retaining device and an anchor that is mechanically coupled to the suture-retaining device. The anchor is affixed to a cortex of the humerus to provide firm support for the suture-retaining device. The suture-retaining device, which is positioned in the intramedullary cavity of the humerus, allows a plurality of sutures to connect the rotator cuff tendon to the anchoring device, and allows suture knots to be located inside the intramedullary cavity.

Figure 1:
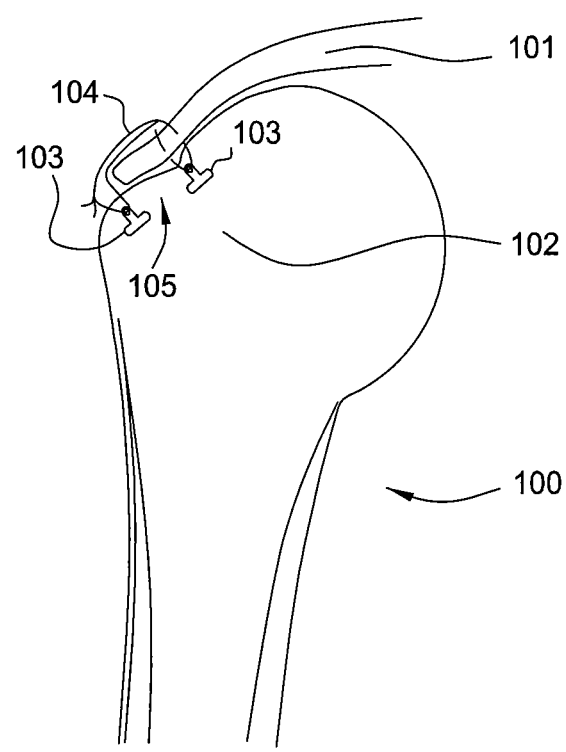
FIG. 1 schematically illustrates a rotator cuff tendon secured to a humeral head of a humerus by a plurality of suture anchors.
Figure 2:
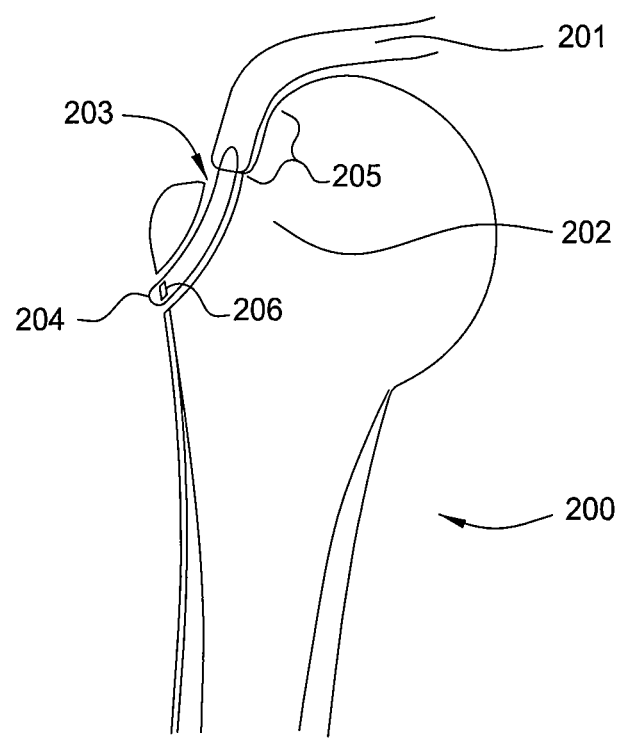
FIG. 2 schematically illustrates a rotator cuff tendon secured to a humeral head of a humerus by a bone tunnel.
Figure 3A:
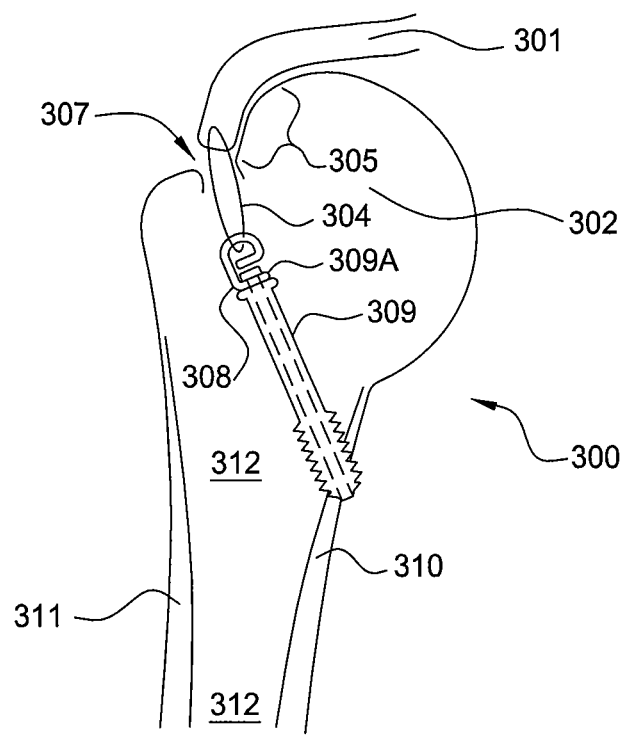
FIGS. 3A and 3B depict a suture-retaining device and anchor for securing a rotator cuff tendon, according to one embodiment of the invention.

The anchor and suture-retaining device according to an embodiment of the invention is positioned in the intramedullary cavity of the humerus after removal of bone material from the humeral head. The removal of the bone material from the humeral head provides access to the intramedullary cavity of the humerus. FIG. 3A depicts a suture-retaining device and anchor for securing the rotator cuff tendon to the humeral head, according to such an embodiment. As shown, a rotator cuff tendon 301 is held against region 305 of humeral head 302. A plurality of sutures 304 are sewn into rotator cuff tendon 301, passed through an opening 307 formed in humeral head 302, looped around a suture-retaining device 308 and tied. For clarity, only one suture 304 is illustrated, but in practice a large number of sutures are used. The sutures 304 may be replaced by any other suitable flexible fastener such as a strap, mesh, or a woven material. Suture-retaining device 308 is a hook or loop configured to accommodate a plurality of sutures, and is mechanically coupled to an anchor 309. In this embodiment, anchor 309 is a bone screw and is threaded into a far cortex 310 of humerus 300. Far cortex 310 is made up of hard bone material and provides a strong base for supporting anchor 309. In this way, anchor displacement due to weak support material is avoided. FIG. 3A depicts anchor 309 inserted into far cortex 310 of humerus 300, but embodiments also contemplate using near diaphyseal cortex 311 as the supporting material for anchor 309, such as shown in FIG. 3B.

Figure 3B:
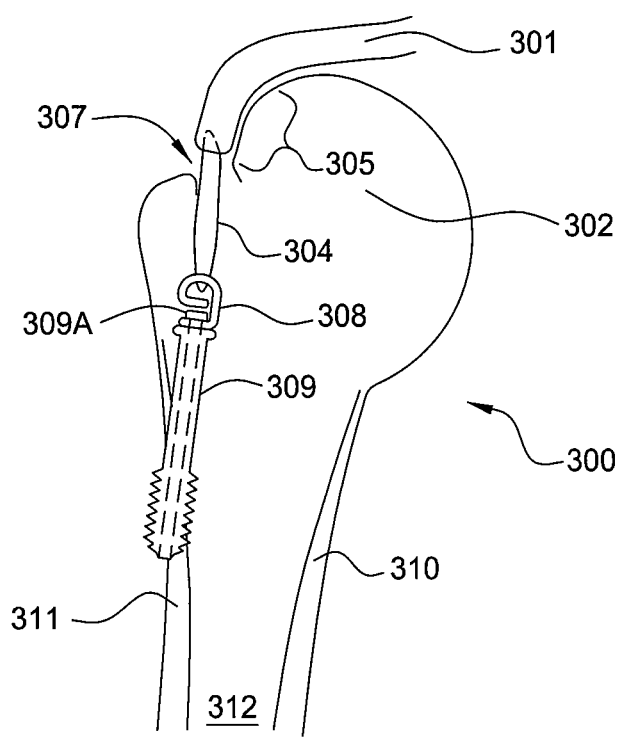

In the embodiment illustrated in FIGS. 3A and 3B, anchor 309 is a bone screw and suture-retaining device 308 is mechanically coupled to anchor 309 by passing the shaft of anchor 309 through an appropriately sized opening in suture-retaining device 308. In this way, the head 309A of anchor 309 acts as a mechanical stop for suture-retaining device 308. Other means of mechanically coupling suture-retaining device 308 to anchor 309 are also contemplated, including threaded attachment and welding. Suture-retaining device 308 may also be integral with anchor 309 so they are physically inseparable during normal use.

The placement of anchor 309 in far cortex 310 reduces the potential for anchor displacement since far cortex 310 consists of strong bone material. In addition, the positioning of anchor 309 and suture-retaining device 308 in intramedullary cavity 312 of humerus 300, as shown, provides a securing force on rotator cuff tendon 301 at a favorable angle. Because of this, lift-off of rotator cuff tendon 301 from region 305 is minimized, even when the arm containing humerus 300 is raised. Lastly, suture-retaining device 308 facilitates the use of a large number of sutures to secure rotator cuff tendon 301 to anchor 309. Therefore, smaller sutures, that result in smaller knot volumes, may be used, and a more robust connection may be established between rotator cuff tendon 301 and anchor 309. For example, a plurality of #0 sutures may be used in place of a single #5 suture.

Figure 4:
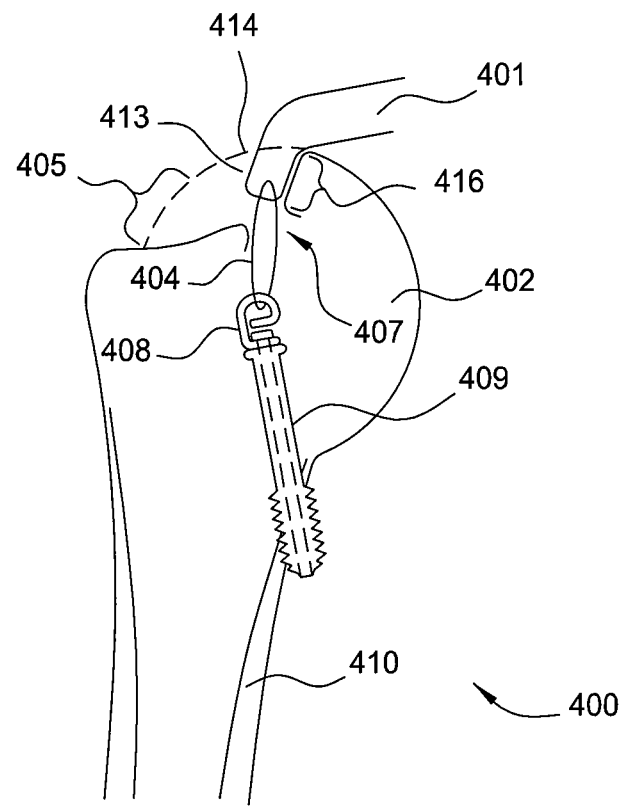
FIG. 4 illustrates an anchor and a suture-retaining device used in conjunction with the removal of a region of humeral head, according to an embodiment of the invention.

The anchor and suture-retaining device according to embodiments of the invention may be positioned in the intramedullary cavity of the humerus after additional removal of bone material from the humeral head. The additional removal of bone material from the humeral head facilitates repair of a rotator cuff tendon that has been substantially shortened and is unable to reach the footprint of humeral head 302. FIG. 4 illustrates an anchor 409 and a suture-retaining device 408 used in conjunction with the removal of a region 413 of humeral head material, according to an embodiment of the invention. The shape of humeral head 402 prior to removal of region 413 is indicated by original surface 414, which is represented as a broken line. Rotator cuff tendon 401, as shown, is too short for reattachment to region 405 of original surface 414. Therefore, region 413 is removed from humeral head 402, and anchor 409 is inserted into cortex 410 of humerus 400. In this configuration, rotator cuff tendon 401 can be secured against surface 416 of humeral head 402 by sewing a plurality of sutures 404 through rotator cuff tendon 401 and securing the sutures 404 to suture-retaining device 408 via an opening 407 formed in humeral head 402. In this embodiment, suture-retaining device 408 and anchor 409 are substantially similar in organization and function to suture-retaining device 308 and anchor 309, respectively, as described above in FIG. 3A. In addition to allowing the repair of a shortened rotator cuff tendon, this embodiment also shares the advantages of the embodiment described above in conjunction with FIG. 3A.

The present invention further contemplates a suture-retaining device and an anchor that is configured to have an adjustable length. With a fixed-length anchor, the final position of the suture anchor point relative to the rotator cuff tendon is determined by how far the anchor is inserted into a cortex of the humerus. In some cases, it may be necessary to penetrate the cortex of the humerus with the anchor to the extent that a substantial portion of the anchor protrudes through the cortex. This could be problematic and may result in complications. In contrast, an adjustable length anchor may be placed at an optimal depth in the cortex of the humerus, and the final position of the suture-retaining device may be set by adjusting the length of the anchor. Hence, this embodiment facilitates fine adjustment of the suture-retaining device position relative to a rotator cuff tendon without screwing the anchor too deeply through a cortex of the humerus.

Figure 5:
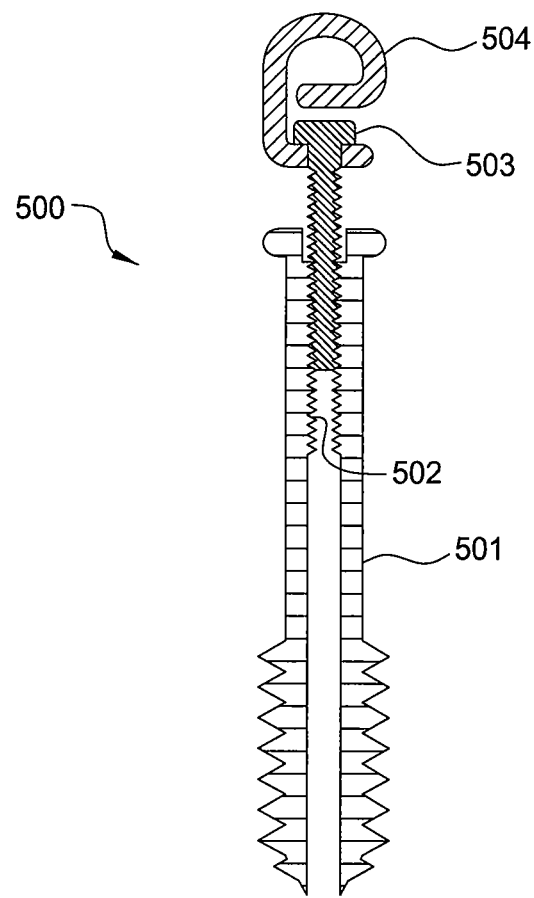
FIG. 5 is a schematic cross-sectional view of an adjustable length anchor, according to an embodiment of the invention.

FIG. 5 is a schematic cross-sectional view of an adjustable length anchor 500, according to an embodiment of the invention. Adjustable length anchor 500 includes a cannulated bone screw 501, which has internal threads 502. Internal threads 502 engage with a secondary screw 503, so that secondary screw 503 may adjust the position of a suture-retaining device 504 as desired. The suture retaining device 504 is movable longitudinally relative to a distal end 505 of the anchor 500. The anchor 500 may be used with any of the systems described herein and all such uses are specifically incorporated.

A suture-retaining device may also have alternative configurations according to the present invention. For example, a suture-retaining device may be configured with a clamp mechanism that allows a plurality of sutures to be secured quickly and simultaneously. One time-consuming aspect of tendon repair is the large number of knots that must be tied when securing a tendon to a suture-retaining device. The knots are a limiting factor in the efficiency of the procedure, and with a clamp mechanism, no suture knots are necessary at all. Further, all sutures may be secured at one time.

Figure 6B:
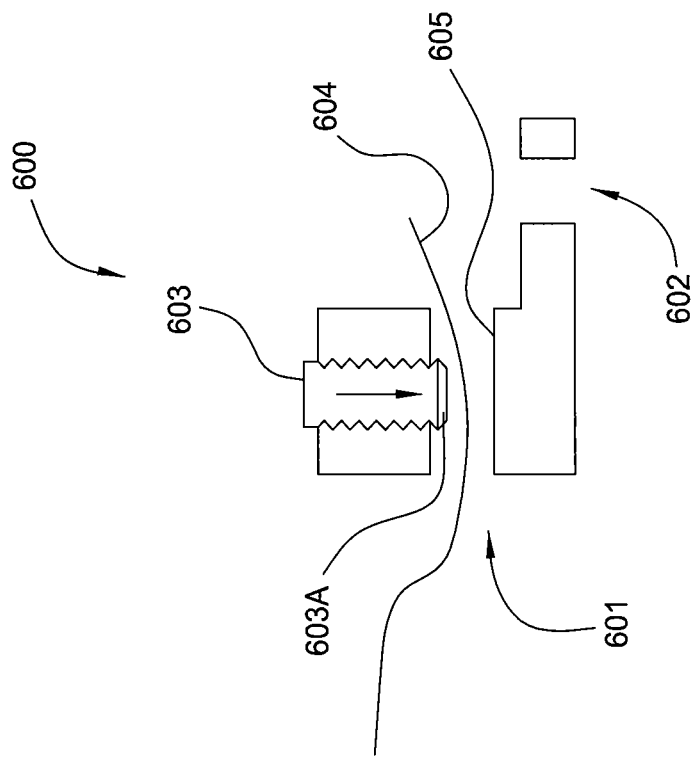
FIG. 6B is a schematic cross-sectional view of a suture-retaining device with a suture passed through a through-hole.
Figure 6A:
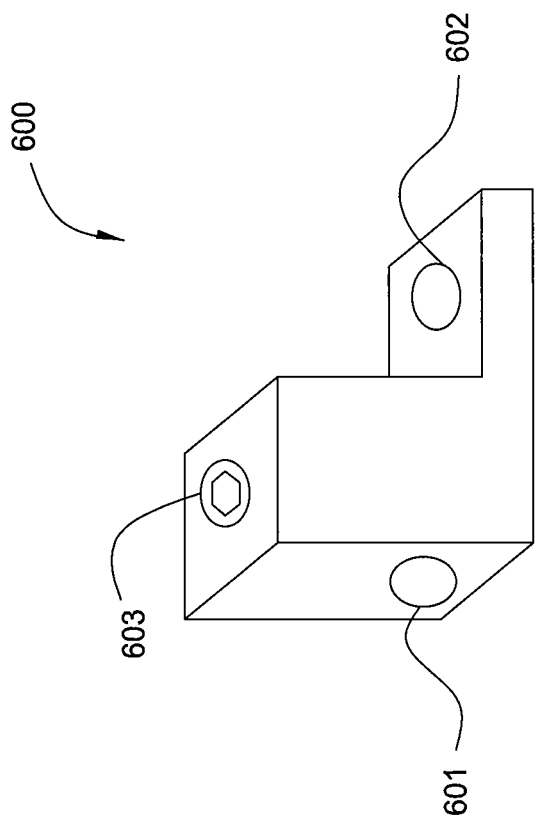
FIG. 6A is a schematic view of a suture-retaining device with a through-hole and clamp mechanism, according to an embodiment of the invention.

FIG. 6A is a schematic view of a suture-retaining device 600 with a through-hole and clamp mechanism. Suture-retaining device 600 includes a through-hole 601, through which one or more sutures are passed. Attachment hole 602 serves as a means for mechanically coupling suture-retaining device 600 to an anchor, such as anchor 309, illustrated in FIGS. 3A and 3B. Hex-head screw 603 may be rotated and moved into through-hole 601 as a clamp to compress sutures positioned therein, obviating the need for suture knots. FIG. 6B is a schematic cross-sectional view of suture-retaining device 600 with a suture 604 passed through through-hole 601. As shown, hex-recess screw 603 may be rotated to move downward against suture 604 and, thus, secure suture 604 to suture-retaining device 600 without the need for a knot. As noted above, a plurality of sutures 604 may be secured by suture-retaining device 600 simultaneously. Alternatively, the clamp mechanism may include a wedge mechanism which, when slid, tightens against the sutures. The wedge mechanism may include a wedge and a screw which, when rotated, slides the wedge, thereby providing the clamping force. The wedge mechanism may also include a self-tightening component, whereby traction on the sutures by the repaired structure serves to slide the wedge in the direction of increased tightening, enhancing or producing the clamping force.

To prevent premature separation of suture 604 from suture-retaining device 600, hex-head screw 603 may be configured to minimize cutting of suture 604. In one embodiment, surface 603A of hex-head screw 603 is made up of relatively compliant material, such as a polymer. Alternatively, most or all of hex-head screw 603 may consist of the compliant material. In this embodiment, it is contemplated that the ratio of the modulus of elasticity of the material making up surface 603A to the modulus of elasticity of compression surface 605 is substantially less than about 0.2. In this way, compression of suture 604 between surface 603A and compression surface 605 is less likely to result in cutting of suture 604.

Figure 6C:
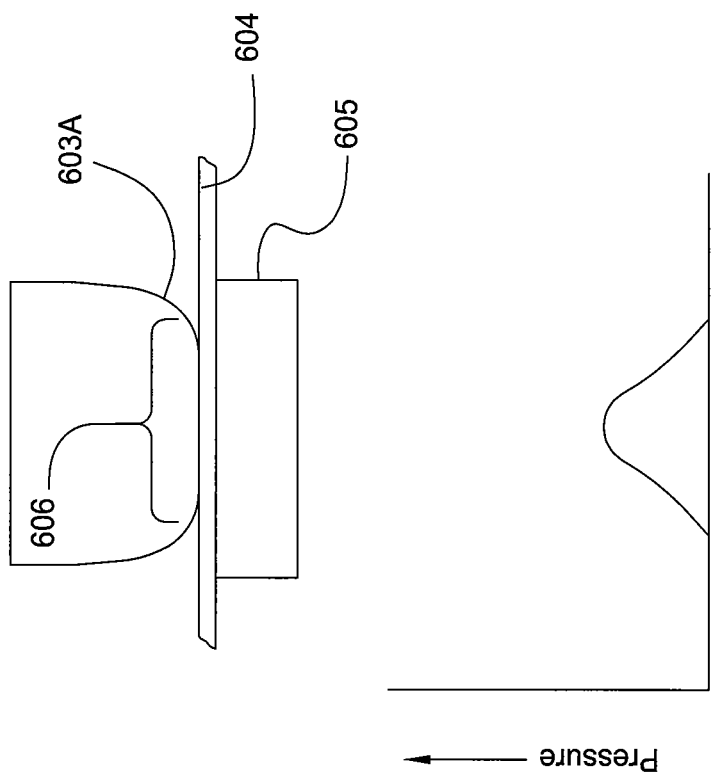
FIG. 6C illustrates a cross-section of two surfaces of a suture-retaining device, as well as the resultant pressure present throughout a suture compressed between the surfaces.

In another embodiment, the cross-section of surface 603A is configured to minimize the pressure gradient experienced by suture 604 when compressed between surface 603A and compression surface 605. A high pressure gradient present on any portion of suture 604, when secured by suture-retaining device 600, might result in cutting of suture 604. Hence, the cross-section of surface 603A is modified to minimize such pressure gradients in suture 604. FIG. 6C illustrates a cross-section of surface 603A and compression surface 605, as well as the resultant pressure present throughout suture 604 when compressed therebetween. As shown, high pressure gradients in suture 604 are additionally avoided by providing surface 603A with a gently tapering profile at the edges of contact region 606. In this embodiment, the profile of surface 603A may be a curve with a gradually changing slope, such as a sinusoidal curve or a section of a circle.

Figure 7:
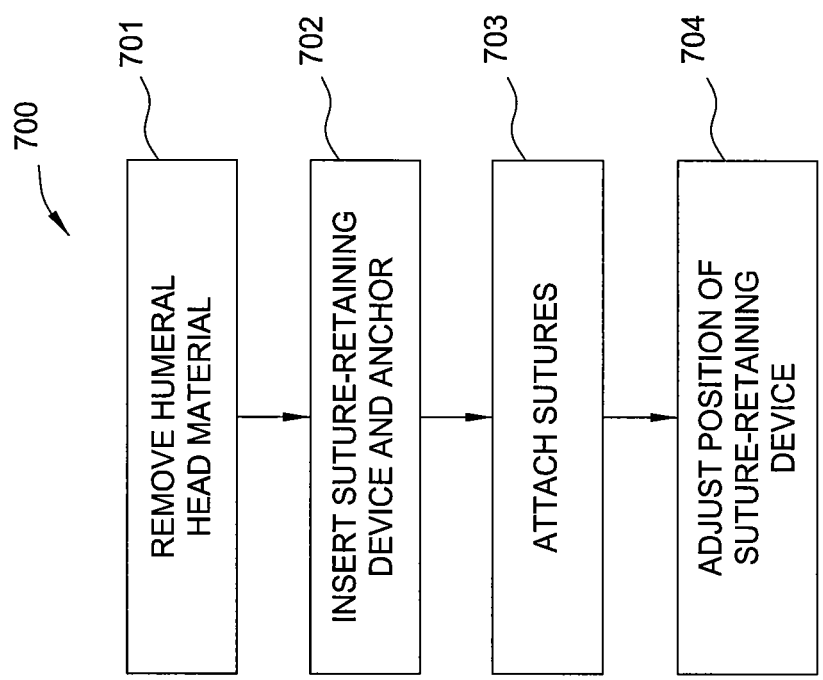
FIG. 7 is a flow chart summarizing a sequence of steps for securing the rotator cuff tendon to the humeral head, according to embodiments of the invention.

FIG. 7 is a flow chart summarizing a sequence of steps 700 for securing the rotator cuff tendon to the humeral head, according to embodiments of the invention. In step 701, a region of humeral head material is removed to provide access to the intramedullary cavity of the humerus and to facilitate optimal placement of the rotator cuff tendon for reattachment. In step 702, a suture-retaining device and anchor are inserted into the intramedullary cavity of the humerus and the anchor is affixed to a cortex of the humerus. The suture-retaining device is mechanically coupled to the anchor prior to insertion of the anchor. Alternatively, the suture-retaining device may be mechanically coupled to the anchor after insertion of the anchor. In step 703, sutures are attached to the rotator cuff tendon as necessary and are secured to the suture-retaining device. The sutures may be individually secured to the suture-retaining device by tying. Alternatively, the sutures may all be secured at one time using a through-hole and clamp mechanism as described above in conjunction with FIG. 6A. In step 704, the final position of the suture-retaining device may be set by adjusting the depth of penetration of the anchor into the cortex. Alternatively, when the anchor is an adjustable length anchor, adjusting the anchor secondary screw may set the final position of the suture-retaining device. In this context, "intramedullary cavity" refers to the space inside the normal surface of the bone and within the cortex of the bone.

FIGS. 8A to 8H depict a suture-retaining device and anchor for securing a rotator cuff tendon with anchor configurations that are different from that shown in FIGS. 3A and 3B. In each of FIGS. 8A-8H, a suture-retaining device and anchor is positioned within an intramedullary cavity 312 of humerus 300 after removal of bone material from the humeral head. As shown, a rotator cuff tendon 301 is held against region 305 of humeral head 302. A plurality of sutures 304 are sewn into rotator cuff tendon 301, passed through an opening formed in humeral head 302, and secured to a suture-retaining device. For clarity, only one suture 304 is illustrated in the figures, but in practice a large number of sutures are used.

Figure 8A:
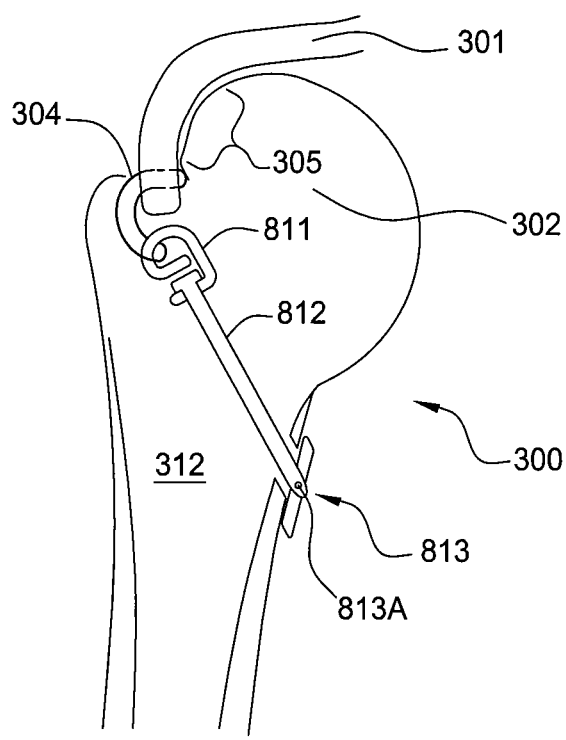
FIGS. 8A to 8H depict a suture-retaining device and anchor for securing a rotator cuff tendon, according alternative embodiments of the invention.

FIG. 8A illustrates a suture-retaining device 811, which is a hook or loop configured to accommodate a plurality of sutures and is mechanically coupled to an anchor 812. Anchor 812 has a toggle bolt 813 that pivots around point 813A of anchor 812. During insertion of anchor 812 into a hole formed in a cortex of the humerus, toggle bolt 813 is pivoted about point 813A so that it is arranged lengthwise along the axis of anchor 812. After insertion, toggle bolt 813 is pivoted to attain the position shown in FIG. 8A. With toggle bolt 813 in this position, anchor 812 provides support for sutures 304 that are tied onto suture-retaining device 811.

Figure 8B:
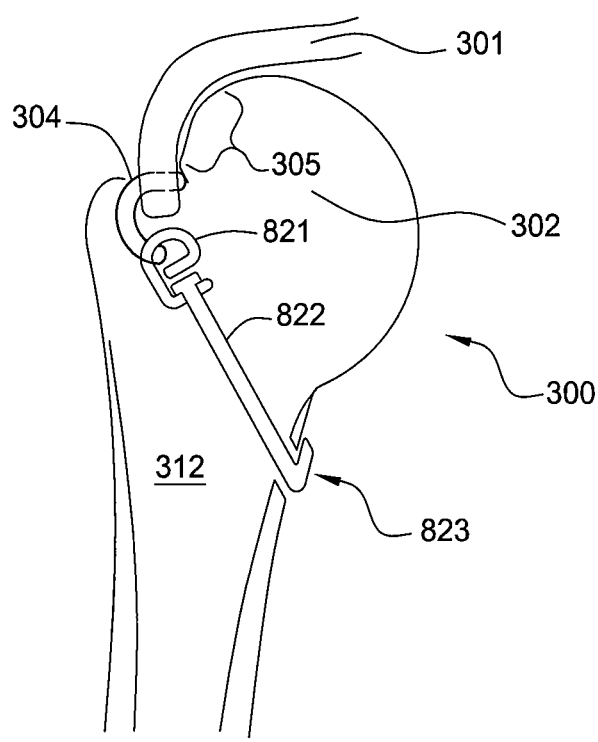

FIG. 8B illustrates a suture-retaining device 821, which is a hook or loop configured to accommodate a plurality of sutures and is mechanically coupled to an anchor 822. Anchor 822 has a hook 823 formed on one end. During insertion of anchor 822 into a hole formed in a cortex of the humerus, anchor 822 is manipulated so that hook 823 can be inserted into the hole and attain the position shown in FIG. 8B. In this position, anchor 822 provides support for sutures 304 that are tied onto suture-retaining device 821.

Figure 8C:
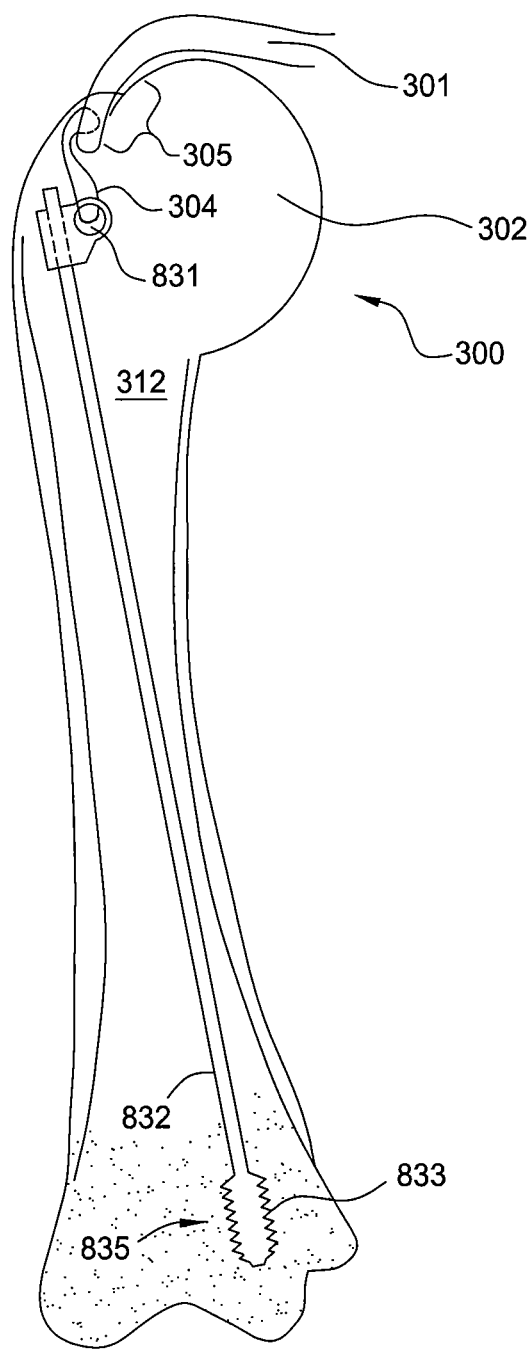

FIG. 8C illustrates a suture-retaining device 831, which is a hook or loop configured to accommodate a plurality of sutures and is mechanically coupled to an anchor 832. Anchor 832 has a length that is slightly less than the length of humerus 300 and has a threaded end 833 that engages with the distal humeral metaphysis. With threaded end 833 affixed to the distal humeral metaphysis, anchor 832 provides support for sutures 304 that are tied onto suture-retaining device 831. Securing the anchor into the distal metaphysis provides some of the same benefits described above concerning securing the anchor into the far cortex. Anchor 832 is also positioned so that a distal end 835 is positioned below the isthmus.

Figure 8D:
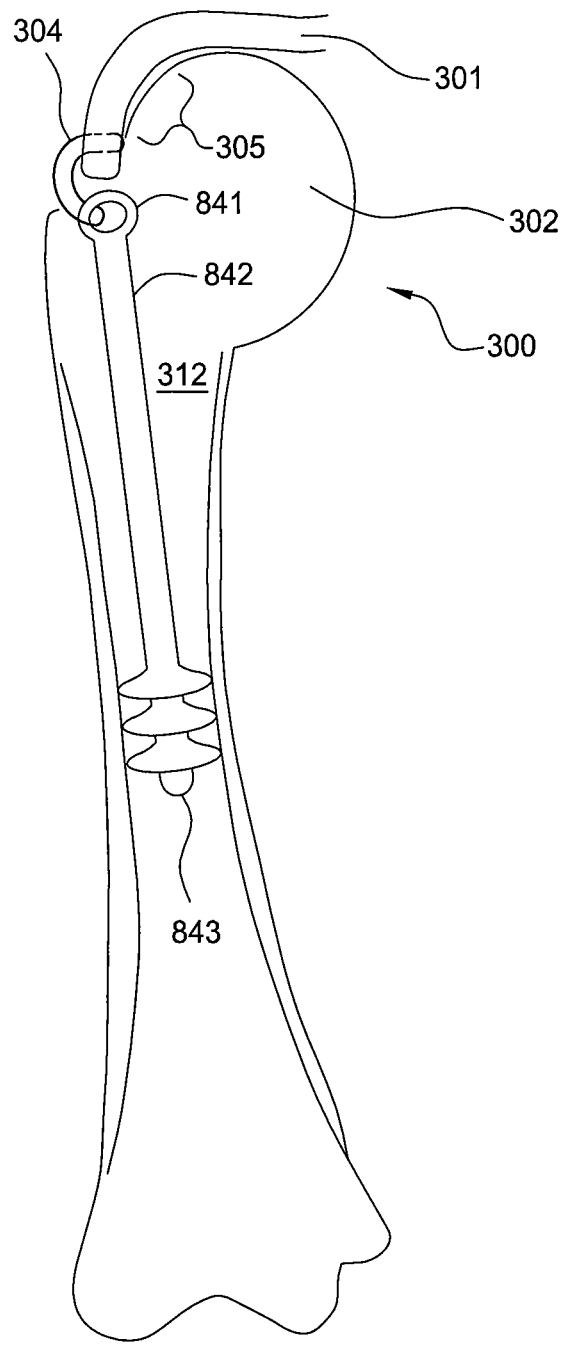

FIG. 8D illustrates a suture-retaining device 841, which is a hook or loop configured to accommodate a plurality of sutures and is formed integrally with an anchor 842. Anchor 842 has a length that is about one-half the length of humerus 300 and has a threaded end 843 that engages with the narrow portion of the endosteal cortex of humerus 300. With threaded end 843 engaged with the narrow portion of the endosteal cortex of humerus 300, anchor 842 provides support for sutures 304 that are tied onto suture-retaining device 841. Stated another way, the anchor 842 contacts an endosteal diameter at the near and far cortex.

Figure 8E:
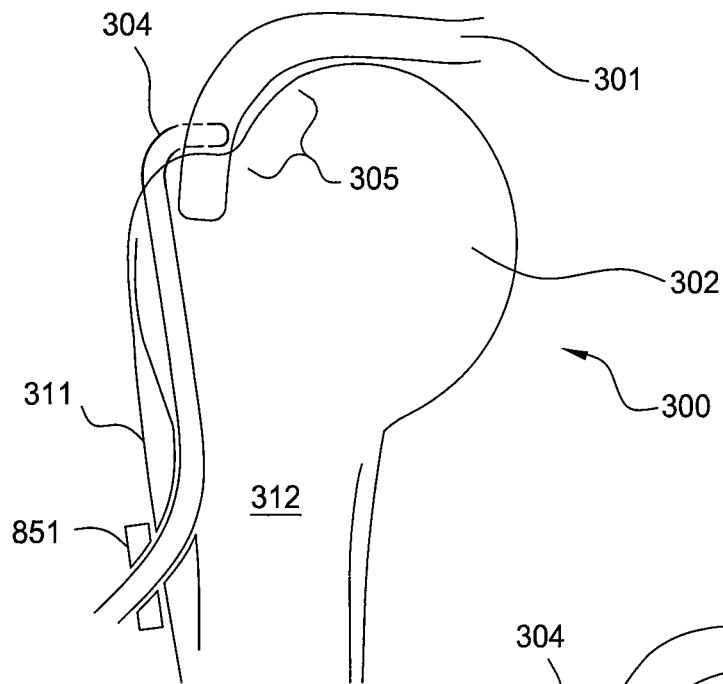

FIG. 8E illustrates an integrated clamp and anchor 851 for securing and supporting a plurality of sutures. Integrated clamp and anchor 851 is configured to have the through-hole and clamp mechanism shown in FIG. 6A but is configured to be positioned on the outer wall of near cortex 311. After sutures 304 are fed through a hole formed in the near cortex 311, integrated clamp and anchor 851 clamps the sutures like the through-hole and clamp mechanism shown in FIG. 6A. The hole in the near cortex 311 is formed to be smaller than integrated clamp and anchor 851 so that integrated clamp and anchor 851, while it is in the position shown in FIG. 8E, can provide support for the sutures that are clamped therein.

The suture retaining device in FIG. 8E can also be made up of an integrated suture-retaining device and anchor which rests on the surface of the bone. Such integrated device may have a means of retaining the suture including one or more holes, fenestration, or irregularities, over which the sutures may be tied. The location of the device in FIG. 8E is chosen to be an area of strong cortex, as illustrated in the sites for anchor engagement in FIGS. 3A and 3B. Because the location is distant from the greater tuberosity, with important nerve, muscle, and vascular structures often lying between this location and the greater tuberosity, the technique of application includes making a separate surgical approach to the bone surface for placement of the integrated suture-retaining device and anchor.

Figure 8F:
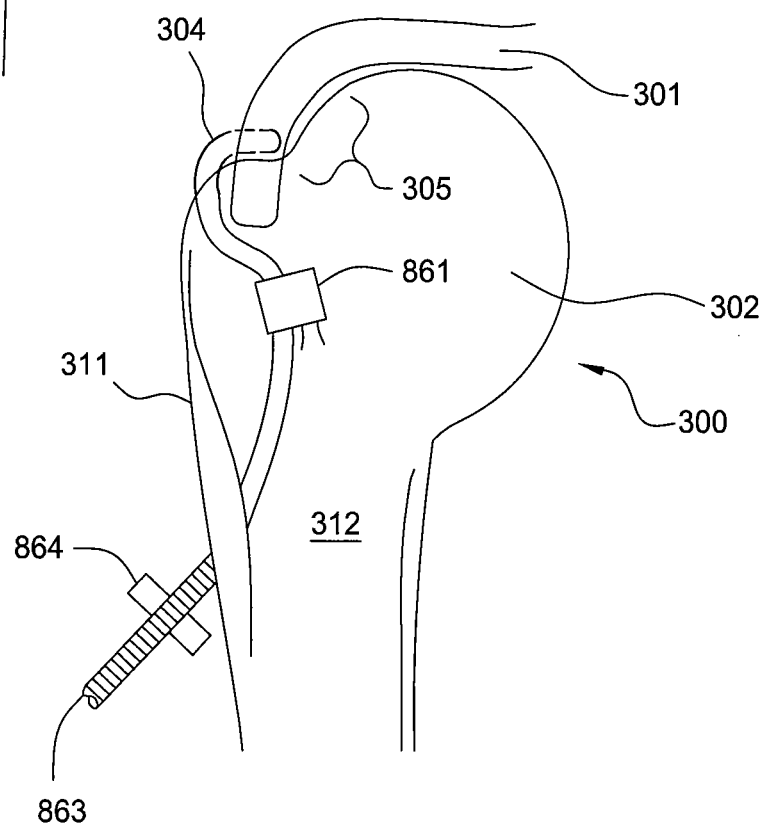

FIG. 8F illustrates a suture-retaining device 861, which is configured to have the through-hole and clamp mechanism shown in FIG. 6A and mechanically coupled to an anchor 862 that has a threaded end 863. After anchor 862 is inserted into a hole formed in a near cortex 311 of the humerus, a nut 864 is rotated and tightened against the outer wall of near cortex 311. Anchor 862, in the position shown in FIG. 8F, provides support for sutures 304 that are secured in suture-retaining device 861.

Figure 8G:
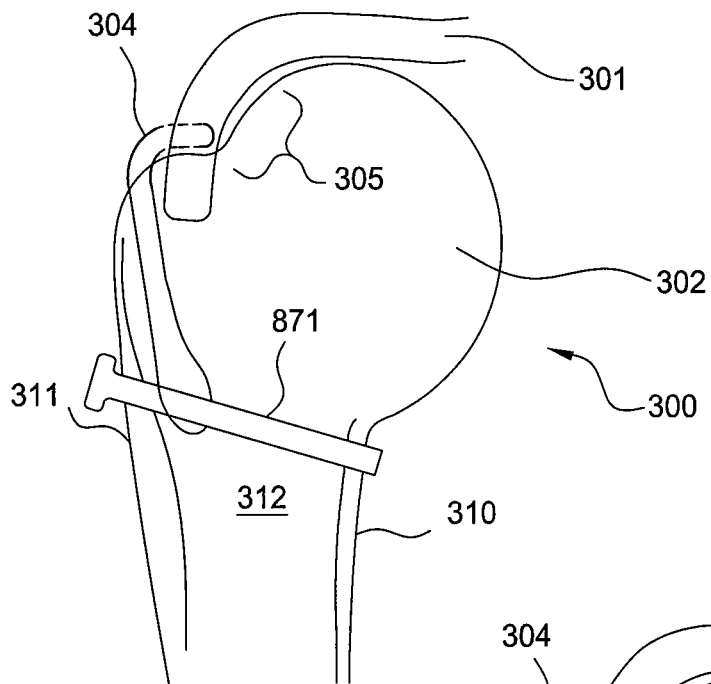

FIG. 8G illustrates a suture-retaining device configured as an anchor element, which may be a transverse bar 871 that is supported in a pair of holes formed respectively in a far cortex 310 of the humerus and a near cortex 311 of the humerus. Sutures 304 are tied onto this transverse bar and the transverse bar provides support for the sutures that are tied thereto.

Figure 8H:
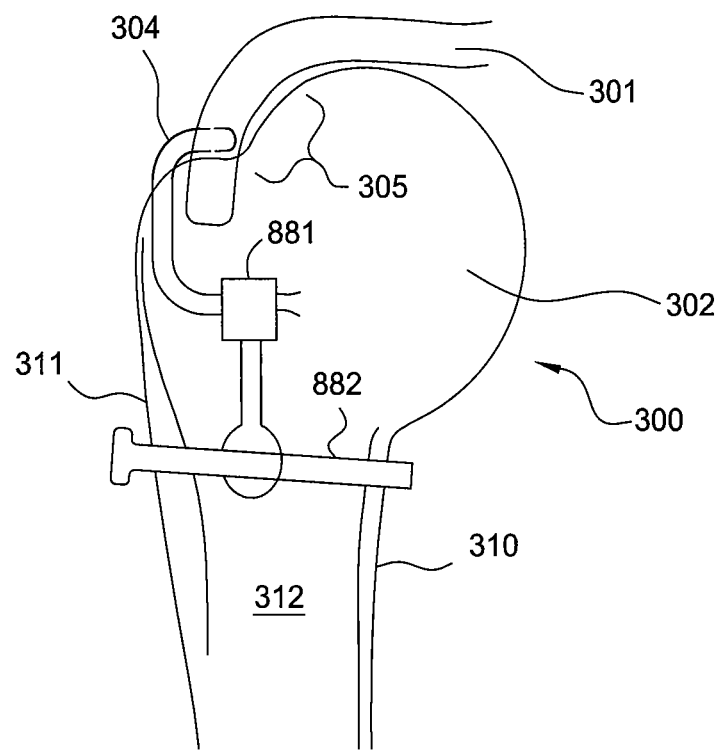

FIG. 8H illustrates a suture-retaining device configured to have the through-hole and clamp mechanism shown in FIG. 6A and mechanically coupled to an anchor element, such as a transverse bar 882 that is supported in a pair of holes formed respectively in a far cortex 310 of the humerus and a near cortex 311 of the humerus. The anchor element provides support for the sutures that are secured in suture-retaining device 881.

While the foregoing is directed to embodiments of the present invention, other and further embodiments of the invention may be devised without departing from the basic scope thereof, and the scope thereof is determined by the claims that follow.

What is claimed is:

1. A method for repairing a rotator cuff tendon that has detached from a head of a humerus, comprising the steps of:
    passing a screw through and entirely past an entry point on the humerus, without fixation of the screw at a location adjacent to the entry point, until the screw contacts a cortex of the humerus from an endosteal side of the cortex;
    inserting the screw in the cortex of the humerus from the endosteal side of the cortex for threaded engagement with the cortex at a point on the cortex of the humerus at which the screw is inserted; and then
    securing one or more sutures that have been sewn into the rotator cuff tendon to a suture-retaining device that is mechanically coupled to the screw,
    wherein the one or more sutures are secured to the anchor at a location within an intramedullary cavity of the humerus, that is not adjacent to the entry point on the humerus and is between the entry point on the humerus and the point on the cortex of humerus at which the screw is inserted.

2. The method according to claim 1, further comprising the step of mechanically coupling the suture-retaining device to the screw prior to the step of inserting.

3. The method according to claim 1, further comprising the step of adjusting the position of the suture-retaining device relative to the point on the cortex of the humerus at which the screw is inserted.

4. The method according to claim 1, wherein the suture-retaining device is a loop and the one or more sutures are secured to the loop by tying.

5. A method of repairing a rotator cuff tendon that has detached from a head of a humerus, comprising the steps of:
    providing one or more sutures and an anchor;
    sewing the one or more sutures into the rotator cuff tendon;
    passing the anchor through an entry point on the humerus, without fixation of the anchor at a location adjacent to the entry point, until the anchor contacts a far cortex of the humerus from an endosteal side of the far cortex, wherein the far cortex lies on an opposite side of the humerus from the entry point on the humerus;
    after the anchor contacts the far cortex, passing the anchor through the far cortex from the endosteal side of the far cortex and directly securing the anchor to the far cortex at an entry point on the far cortex and an exit point on the far cortex where the anchor passed through the far cortex; and
    securing the one or more sutures to the anchor after the one or more sutures have been sewn into the rotator cuff tendon,
    wherein the one or more sutures are secured to the anchor at a location within an intramedullary cavity of the humerus, that is not adjacent to the entry point on the humerus and is between the entry point on the humerus and the exit point on the far cortex.

6. The method of claim 5, wherein:
the one or more sutures are secured to the anchor after the anchor has been secured to the far cortex.

7. The method of claim 5, further comprising the step of:
forming a hole in the head of the humerus extending to the far cortex from the entry point; and
inserting the anchor into the hole after the one or more sutures have been sewn into the rotator cuff tendon.

8. The method of claim 5, wherein:
the providing step is carried out with the anchor being a screw.

* * * * *